(12) United States Patent
Sakami

(10) Patent No.: US 8,851,745 B2
(45) Date of Patent: Oct. 7, 2014

(54) HYGROMETER AND DEW-POINT INSTRUMENT

(75) Inventor: Shinichirou Sakami, Osaka (JP)

(73) Assignee: Espec Corp., Osaka (JP)

( * ) Notice: Subject to any disclaimer, the term of this patent is extended or adjusted under 35 U.S.C. 154(b) by 310 days.

(21) Appl. No.: 13/557,531

(22) Filed: Jul. 25, 2012

(65) Prior Publication Data

US 2012/0287961 A1    Nov. 15, 2012

Related U.S. Application Data

(62) Division of application No. 12/450,216, filed as application No. PCT/JP2008/055751 on Mar. 26, 2008, now Pat. No. 8,348,500.

(30) Foreign Application Priority Data

Apr. 4, 2007    (JP) ................................. 2007-098022

(51) Int. Cl.
| | |
|---|---|
| *G01N 25/26* | (2006.01) |
| *G01N 25/66* | (2006.01) |
| *G01N 25/56* | (2006.01) |
| *G01N 25/64* | (2006.01) |

(52) U.S. Cl.
CPC ................ *G01N 25/64* (2013.01); *G01N 25/66* (2013.01); *G01N 25/56* (2013.01)
USPC ............... 374/28; 374/16; 374/148; 374/145; 374/208; 73/73; 73/29.01; 73/29.02; 73/866.5

(58) Field of Classification Search
USPC ......... 374/4, 5, 10, 100, 16, 27, 28, 141, 147, 374/148, 29, 43, 145; 73/73, 29.01, 29.02
See application file for complete search history.

(56) References Cited

U.S. PATENT DOCUMENTS

| | | |
|---|---|---|
| 3,661,724 A | 5/1972 | Strickler |
| 4,008,615 A | 2/1977 | MacMaster |
| 4,586,342 A | 5/1986 | Morishita et al. |
| 4,826,327 A | 5/1989 | Michell |
| 4,946,288 A | 8/1990 | Siska et al. |

(Continued)

FOREIGN PATENT DOCUMENTS

| | | |
|---|---|---|
| DE | 10 2005 048 756 | 4/2007 |
| EP | 1938092 | 2/2006 |

(Continued)

*Primary Examiner* — Gail Kaplan Verbitsky
(74) *Attorney, Agent, or Firm* — Gerald E. Hespos; Michael J. Porco; Matthew T. Hespos

(57) ABSTRACT

A hygrometer and dew-point instrument is provided that is structurally simple while reducing the workload during maintenance. The hygrometer measures relative humidity of a measurement space, and has a main body that encapsulates a working fluid therein and causes a heat-pipe phenomenon. The main body is disposed across the measurement space and an external space spaced from the measurement space by a heat-insulating part and has a temperature lower than the measurement space. A first temperature deriving part derives the temperature of the main body in a section where the working fluid evaporates. A space temperature detecting unit detects the temperature of the measurement space. A computation unit calculate relative humidity of the measurement space based on the temperature of the main body derived by the first temperature deriving part and the temperature of the measurement space detected by the space temperature detecting unit.

6 Claims, 6 Drawing Sheets

(56) References Cited

U.S. PATENT DOCUMENTS

| | | | |
|---|---|---|---|
| 5,024,532 A | 6/1991 | Rall | |
| 5,651,498 A | 7/1997 | Meyer et al. | |
| 5,783,747 A * | 7/1998 | Lindow et al. | 73/61.41 |
| 6,092,925 A | 7/2000 | Nojiri | |
| 7,147,368 B2 * | 12/2006 | Chien | 374/147 |
| 7,445,385 B2 * | 11/2008 | Lin | 374/147 |
| 8,083,398 B2 | 12/2011 | Doll | |
| 2004/0008749 A1 * | 1/2004 | Tsang et al. | 374/16 |
| 2004/0146085 A1 | 7/2004 | Lindner et al. | |
| 2006/0256834 A1 * | 11/2006 | Chang et al. | 374/5 |
| 2007/0006995 A1 | 1/2007 | Lin | |

FOREIGN PATENT DOCUMENTS

| | | |
|---|---|---|
| JP | 61-75235 | 4/1986 |
| JP | 61-124860 | 6/1986 |
| JP | 63-259440 | 10/1988 |
| JP | 3021853 | 12/1995 |
| JP | 2003-194756 | 7/2003 |
| JP | 2005-291889 | 10/2005 |

* cited by examiner

HYGROMETER AND DEW-POINT INSTRUMENT

CROSS-REFERENCE TO RELATED APPLICATIONS

This application is a divisional of U.S. patent application Ser. No. 12/450,216 filed on Sep. 21, 2009.

BACKGROUND OF THE INVENTION

1. Field of the Invention

The present invention relates to a hygrometer and a dew-point instrument.

2. Description of the Related Art

Various hygrometers for measuring the humidity of the atmosphere are known. For example, Japanese Utility Model Registration No. 3021853 below discloses a hygrometer for measuring the humidity by using a wet and dry bulb. In this hygrometer, a dry-bulb temperature sensor and a wet-bulb temperature sensor of the same type are installed parallel to each other, a tank with water therein is placed below the wet-bulb temperature sensor, and the sensing part of the wet-bulb temperature sensor is covered with a wick made of gauze or the like impregnated with water of the tank. This hygrometer is configured to obtain a relative humidity from the difference between the dry-bulb temperature shown by the dry-bulb temperature sensor and the wet-bulb temperature shown by the wet-bulb temperature sensor.

Japanese Patent Application Publication No. 2003-194756 discloses a mirror-surface condensing dew-point instrument. This mirror-surface condensing dew-point instrument is based on the principle in which when the surface temperature of the reflecting mirror goes below the dew point of measuring gas, the optical reflectance of the surface of the reflecting mirror is reduced by dew condensation. The dew point of the measuring gas is determined by comparing the received amount of reference light that passes through the measuring gas without being reflected on the reflecting mirror, with the received amount of measuring light reflected on the reflecting mirror while passing through the measuring gas.

Specifically, in this dew-point instrument, the measuring gas is sent into the housing, and the reference light travels straight from the first light source element outside the housing to the measuring optical path inside the housing via the optical fiber, and thereafter reaches the first light receiving element outside the housing via the optical fiber again. On the other hand, the measuring light is introduced from the second light source element outside the housing into the housing via the optical fiber, is then reflected on the mirror surface of the reflecting mirror inside the housing, and thereafter reaches the second light receiving element outside the housing via the optical fiber again. The reflecting mirror has a heat pump, the cooling capacity of which is controlled by the control circuit. The reflecting mirror is cooled by this heat pump, and when the moisture within the measuring gas contacting the reflecting mirror builds up condensation on the mirror surface, the amount of light received by the second light receiving element is reduced. Then, cooling of the reflecting mirror performed by the heat pump is controlled such that the amount of light received by the second light receiving element is reduced relative to the amount of light received by the first light receiving element and such that the amount of light received by the second light receiving element becomes constant. The mirror surface temperature of the reflecting mirror is measured by the temperature detector when the amount of light received by the second light receiving element becomes constant, whereby the dew point is obtained.

However, in the hygrometer described in Japanese Utility Model Registration No. 3021853, because the force for pumping up the water is weakened when the wick becomes old and tainted, a troublesome work for replacing the wick needs to be performed each time. Therefore, there is a problem that the workload of maintaining the hygrometer increases.

The dew-point instrument described in Japanese Patent Application Publication No. 2003-194756, on the other hand, is configured by a large number of constituent parts including the two light source elements, two light receiving elements, plurality of optical fibers, reflecting mirror, heat pump, temperature detector, heat pump control circuit, temperature measuring circuit and so on. The problem therefore is that the structure of this dew-point instrument is complicated.

SUMMARY OF THE INVENTION

The present invention was contrived in order to solve the problems described above, and an object thereof is to provide a hygrometer and a dew-point instrument that can be structurally simplified while reducing the workload of their maintenance.

In order to achieve the object described above, a hygrometer according to the present invention is a hygrometer for measuring a relative humidity of a measurement space, the hygrometer having: a main body part that is configured to encapsulate a working fluid therein and to cause a heat-pipe phenomenon and is disposed across the measurement space and an external space that is spaced from the measurement space by a heat-insulating part and has a temperature lower than that of the measurement space; first temperature deriving part for deriving a temperature of the main body part in a section where the working fluid evaporates; a space temperature detecting unit for detecting a temperature of the measurement space; and a computation unit for calculating the relative humidity of the measurement space based on the temperature of the main body part derived by the first temperature deriving part and the temperature of the measurement space detected by the space temperature detecting unit.

The hygrometer according to the present invention is a hygrometer for measuring a relative humidity of the measurement space, the hygrometer having: a main body part that is installed in the measurement space and configured to encapsulate a working fluid therein and to cause a heat-pipe phenomenon; a heat-insulating part fitted externally to the main body part; a cooling part for cooling a base side part on one side of the main body part in relation to the heat-insulating part and thereby condensing the working fluid that evaporates into gas in a front side part on the other side of the main body part in relation to the heat-insulating part; first temperature deriving part for deriving a temperature of the main body part in a section where the working fluid evaporates; a space temperature detecting unit for detecting a temperature of the measurement space; and a computation unit for calculating the relative humidity of the measurement space based on the temperature of the main body part derived by the first temperature deriving part and the temperature of the measurement space detected by the space temperature detecting unit.

The dew-point instrument according to the present invention is a dew-point instrument for measuring a dew point of the measurement space, the dew-point instrument having: a main body part that is configured to encapsulate a working fluid therein and to cause a heat-pipe phenomenon and is disposed across the measurement space and an external space that is spaced from the measurement space by a heat-insulating part and has a temperature lower than that of the measurement space; and first temperature deriving part for deriving a temperature of the main body part in a section where the working fluid evaporates.

The dew-point instrument according to the present invention is a dew-point instrument for measuring a dew point of a measurement space, the dew-point instrument having: a main body part that is installed in the measurement space and configured to encapsulate a working fluid therein and to cause a heat-pipe phenomenon; a heat-insulating part fitted externally to the main body part; a cooling part for cooling a base side part on one side of the main body part in relation to the heat-insulating part and thereby condensing the working fluid that evaporates into gas in a front side part on the other side of the main body part in relation to the heat-insulating part; and first temperature deriving part for deriving a temperature of the main body part in a section where the working fluid evaporates.

DETAILED DESCRIPTION OF THE PREFERRED EMBODIMENTS

Embodiments of the present invention are described hereinafter with reference to the drawings.

(First Embodiment)

First, a hygrometer according to the first embodiment of the present invention is described with reference to FIGS. 1 and 2.

Figure 1:
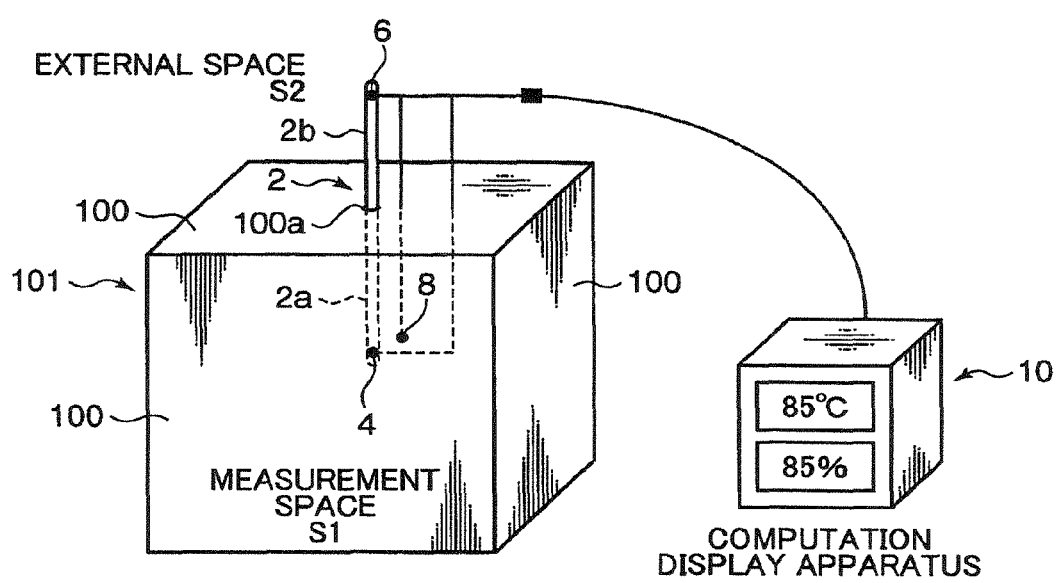
FIG. 1 is a diagram schematically showing the structure of a hygrometer according to a first embodiment of the present invention.
Figure 2:
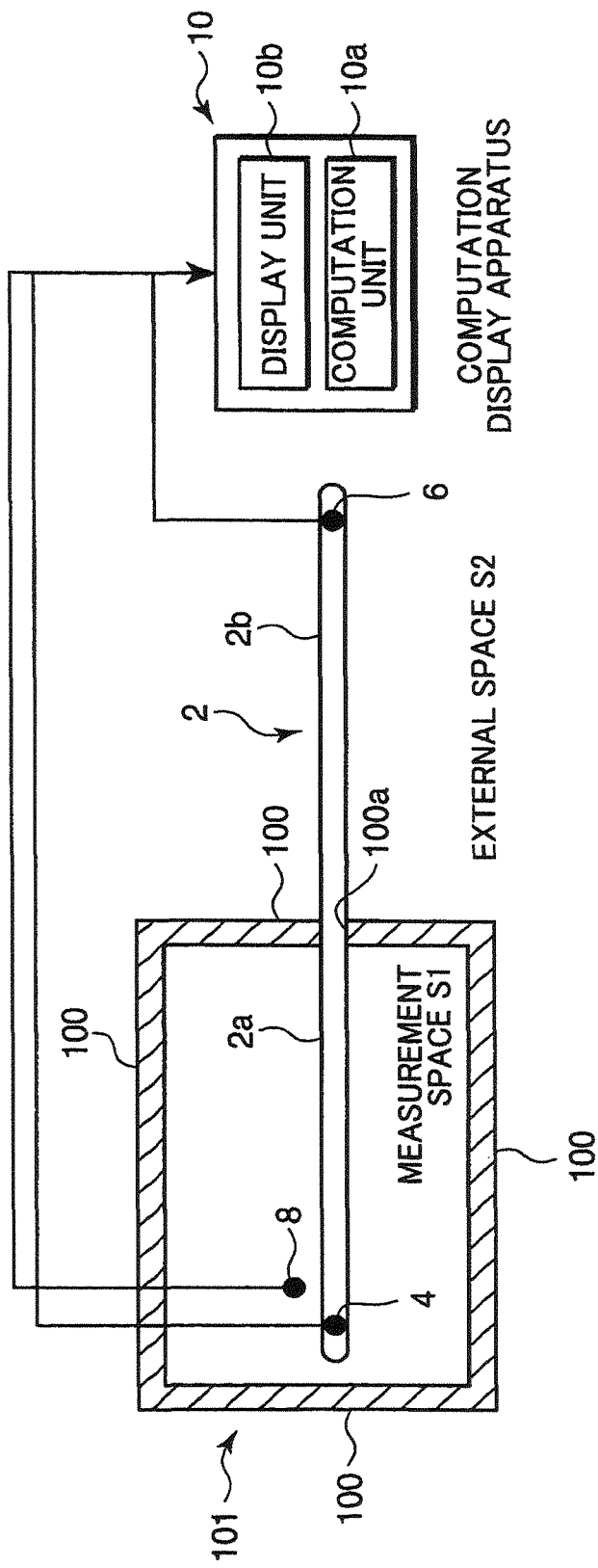
FIG. 2 is a block diagram for explaining the functions of the hygrometer shown in FIG. 1.

The hygrometer according to the first embodiment is for measuring a relative humidity of a measurement space S1 and has a main body part 2, a first external surface temperature sensor 4, a second external surface temperature sensor 6, a space temperature sensor 8, and computation display apparatus 10, as shown in FIG. 1.

The main body part 2 is configured by a heat pipe. The main body part 2 is configured to encapsulate therein water as a working fluid in a pressure-reduced state and to cause a heat-pipe phenomenon. The heat-pipe phenomenon here means a phenomenon in which the heat of the working fluid is transmitted as the working fluid transits from the evaporation phase to the condensation phase, by repeating evaporation and condensation of the encapsulated working fluid in a predetermined place.

The main body part 2 is disposed across the measurement space S1 and an external space S2 outside the measurement space S1. The part of the main body part 2 that is disposed inside the measurement space S1 is referred to as an internal part 2a, and the part disposed in the external space S2 is referred to as an external part 2b. The measurement space S1 is, for example, a space inside a temperature and humidity chamber 101 and is surrounded by a heat-insulating wall 100 (heat-insulating part). The external space S2, on the other hand, is a space outside the temperature and humidity chamber 101. The temperature of the measurement space S1 can be made higher than the temperature of the external space S2 by driving the temperature and humidity chamber 101. The heat-insulating wall 100 configuring a ceiling wall part of the temperature and humidity chamber 101 has a through-hole 100a formed thereon. The main body part 2 is inserted into the through-hole 100a and accordingly installed to extend across the measurement space S1 and the external space S2 spaced by the heat-insulating wall 100, as described above. Accordingly, the working fluid evaporates within the internal part 2a of the main body part 2, while the working fluid formed into gas is condensed within the external part 2b. Note that the main body part 2 may be disposed not only in a vertical position but also in an inclined position inclined on some level from the vertical position, as long as the heat-pipe phenomenon can be caused.

The first external surface temperature sensor 4 is attached to an external surface in the vicinity of an end part of the internal part 2a of the main body part 2 disposed inside the measurement space S1. Specifically, the first external surface temperature sensor 4 is attached to an external surface of a section of the internal part 2a where the liquid working fluid accumulates when the heat-pipe phenomenon is caused completely in the main body part 2. Specifically, when the heat-pipe phenomenon is started in the main body part 2, the liquid working fluid accumulated in the internal part 2a evaporates gradually, and consequently the fluid level of the working fluid is lowered. When the heat-pipe phenomenon is completely caused in the main body part 2, the fluid level of the working fluid becomes the lowest. It is preferred that the first external surface temperature sensor 4 be positioned below the fluid level of the working fluid at this moment and be attached within a range where the liquid working fluid is accumulated. The first external surface temperature sensor 4 detects the external surface temperature of the section where the first external surface temperature sensor 4 is attached, and then outputs a signal corresponding to the result of the detection. Because the external surface temperature of the section where the first external surface temperature sensor 4 is attached equals to the dew-point temperature of the measurement space S1 as described hereinafter, the first external surface temperature sensor 4 outputs a signal corresponding to the dew-point temperature of the measurement space S1. In other words, in the first embodiment, the first external surface temperature sensor 4 functions as the first temperature deriving part of the present invention.

The second external surface temperature sensor 6 functions as second temperature deriving part of the present invention and is attached to an external surface in the vicinity of an end part of the external part 2b of the main body part 2 disposed in the external space S2. Specifically, the second external surface temperature sensor 6 is attached to an external surface of a section of the external part 2b where the working fluid in the form of gas is condensed, when the heat-pipe phenomenon is caused in the main body part 2. The second external surface temperature sensor 6 detects the external surface temperature of the section where the second external surface temperature sensor 6 is attached, and then outputs a signal corresponding to the result of the detection.

The space temperature sensor 8 functions as the space temperature detecting unit of the present invention. This space temperature sensor 8, which is disposed within the measurement space S1, detects the temperature of the measurement space S1 and outputs a signal corresponding to the result of the detection.

The computation display apparatus 10 computes the relative humidity of the measurement space S1 and displays the calculated relative humidity and the temperature of the measurement space S1. The signal that is output from the first external surface temperature sensor 4, the signal that is output from the second external surface temperature sensor 6, and the signal that is output from the space temperature sensor 8 are input to this computation display apparatus 10. The computation display apparatus 10 has a computation unit 10a and a display unit 10b, as shown in FIG. 2.

The computation unit 10a calculates the relative humidity of the measurement space S1 from each of the signals input to the computation display apparatus 10. Specifically, the computation unit 10a calculates the relative humidity of the measurement space S1 on the basis of the signal from the first external surface temperature sensor 4 and the signal from the space temperature sensor 8, as described hereinafter. Moreover, on the basis of the signal from the first external surface temperature sensor 4 and the signal from the second external surface temperature sensor 6, the computation unit 10a calculates the temperature difference between the external surface temperature of the section of the internal part 2a where the working fluid evaporates and the external surface temperature of the section of the external part 2b where the gaseous working fluid is condensed.

The display unit 10b displays the relative humidity of the measurement space S1 in response to the results of the calculation performed by the computation unit 10a, and displays the temperature of the measurement space S1 on the basis of the signal from the space temperature sensor 8.

Next, operations of the hygrometer according to the first embodiment are described.

In the hygrometer according to the first embodiment, the moisture existing in the measurement space S1 adheres to the internal part 2a of the main body part 2 disposed within the measurement space S1 and condenses, whereby the heat-pipe phenomenon is caused in the main body part 2. Specifically, the condensation heat generated by the condensation of the moisture on the external surface of the internal part 2a causes the working fluid to evaporate in the internal part 2a, and thus obtained gaseous working fluid flows toward the external part 2b of the main body part 2 at substantially sonic speed. In the external part 2b, on the other hand, the gaseous working fluid is cooled and condensed due to the fact that the external space S2 is colder than the measurement space S1, and thus obtained liquid working fluid flows toward the internal part 2a. By repeating the evaporation and condensation of the working fluid in a predetermined section of the main body part 2 as described above, the heat of the working fluid is transmitted as the working fluid transits from the section where it evaporates to the section where it is condensed.

When the heat-pipe phenomenon is completely caused in the main body part 2, the difference between the external surface temperature of the internal part 2a and the external surface temperature of the external part 2b becomes constant. Then, on the basis of the signal from the first external surface temperature sensor 4 and the signal from the second external surface temperature sensor 6, the computation unit 10a calculates the temperature difference between the external surface temperature of the section of the internal part 2a where the working fluid evaporates and the external surface temperature of the section of the external part 2b where the gaseous working fluid is condensed. It is possible to confirm from the calculated temperature difference that the heat-pipe phenomenon is completely caused in the main body part 2.

Figure 3:
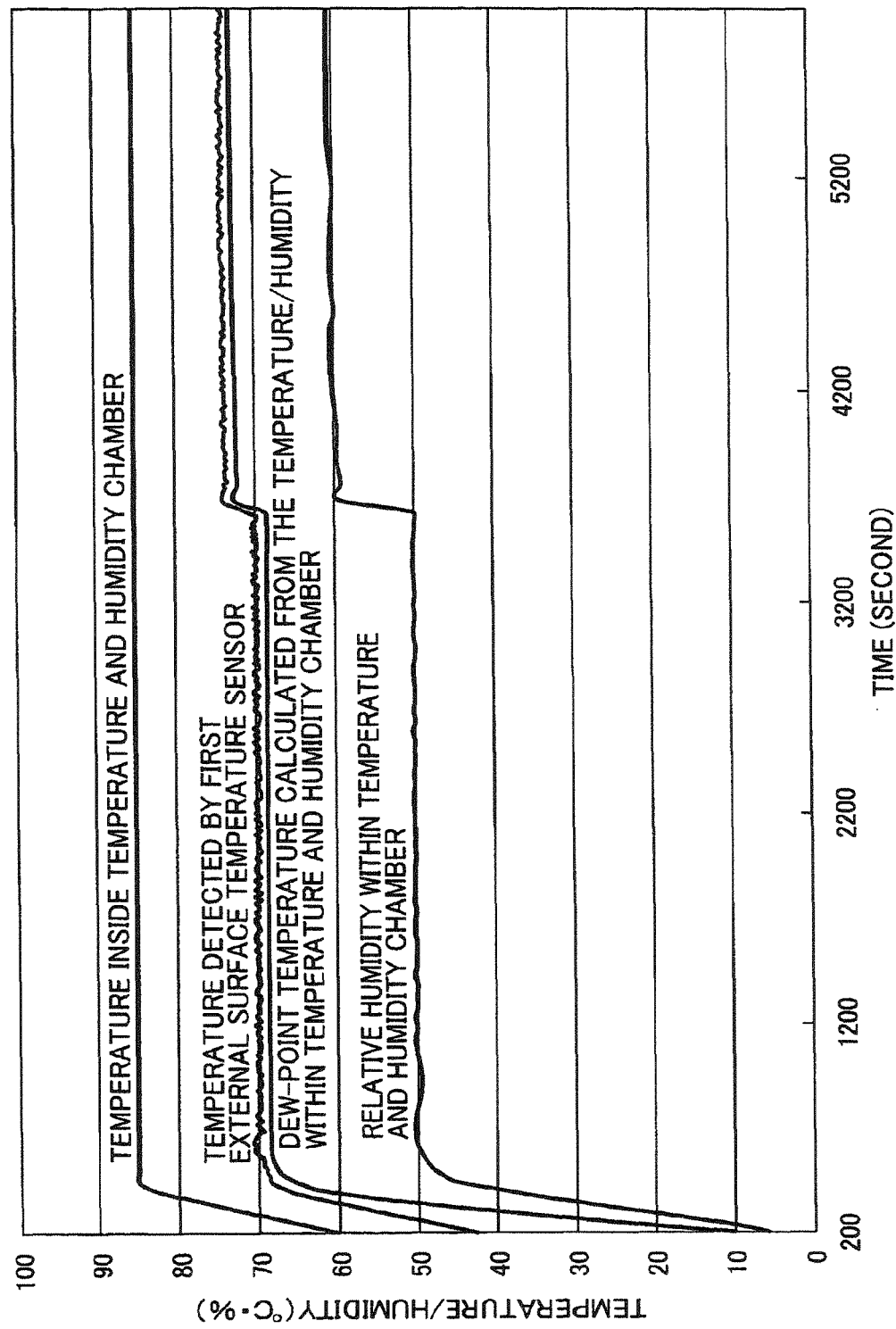
FIG. 3 is a diagram showing the results of the temperature detected by a first external surface temperature sensor of the hygrometer according to the first embodiment.

Here, FIG. 3 shows the results of the detection of the external surface temperature of the internal part 2a that is obtained by the first external surface temperature sensor 4. FIG. 3 shows, sequentially, the external surface temperature of the section of the internal part 2a where the liquid working fluid accumulates, the external surface temperature being actually detected by the first external surface temperature sensor 4, the temperature and the relative humidity of the measurement space S1 that are measured by the temperature and humidity chamber 101, and the dew point of the measurement space S1 calculated from the temperature and the relative humidity. These measurements are conducted under the condition that the heat-pipe phenomenon is caused completely in the main body part 2. It is understood from the results shown in FIG. 3 that the external surface temperature that is actually detected by the first external surface temperature sensor 4 in the section of the main body part 2 where the liquid working fluid accumulates and where the heat-pipe phenomenon is caused, that is, the section where the working fluid evaporates, is substantially equal to the dew point of the measurement space S1 that is calculated from the temperature and relative humidity of the measurement space S1 that are measured by the temperature and humidity chamber 101. As a result, it was discovered, in the main body part 2 where the heat-pipe phenomenon is caused, that the dew point of the measurement space S1 could be derived by causing the first external surface temperature sensor 4 to detect the external surface temperature of the section where the working fluid accumulates, the section being a part of the internal part 2a disposed in the measurement section S1.

The signal indicating the result of the detection by the first external surface temperature sensor 4, that is, the signal showing the dew-point temperature of the measurement space S1, as well as the signal indicating the result of the detection by the space temperature sensor 8, that is, the signal showing the temperature of the measurement space S1, are input to the computation unit 10a, and the relative humidity of the measurement space S1 is calculated based on these signals. Then, the display unit 10b displays the relative humidity of the measurement space S1 calculated by the computation unit 10a and the temperature of the measurement space S1 detected by the space temperature sensor 8.

As described above, in the hygrometer according to the first embodiment, the main body part 2 causing the heat-pipe phenomenon is disposed across the measurement space S1 and the external space S2 that are spaced from each other by the heat-insulating wall 100, and the external space S2 is colder than the measurement space S1. For this reason, the external surface temperature of the section on the measurement space S1 side of the main body part 2 where the working fluid evaporates is substantially equal to the dew point of the measurement space S1. Then, because the external surface temperature of the section where the working fluid evaporates is detected by the first external surface temperature sensor 4, the computation unit 10a can calculate the relative humidity of the measurement space S1 on the basis of the detected external surface temperature of the section where the working fluid evaporates, and the temperature of the measurement space S1 that is detected by the space temperature sensor 8. Unlike a conventional wet and dry bulb hygrometer, because the hygrometer of the first embodiment does not require a wick for humidity measurement, it is not necessary to carry out the troublesome work for replacing the wick every time when the wick becomes old and the force for pumping up the water is weakened. Therefore, the workload of maintaining the hygrometer can be alleviated.

Unlike the conventional mirror-surface condensing dew-point instrument configured by a large number of constituent parts, the hygrometer according to the first embodiment can be structurally simplified because it is configured by the main body part 2 where the heat-pipe phenomenon is caused, the first external surface temperature sensor 4, the second external surface temperature sensor 6, the space temperature sensor 8, and the computation display apparatus 10. Therefore, the hygrometer according to the first embodiment can be structurally simplified, while alleviating the workload of its maintenance.

In the hygrometer according to the first embodiment, because the first external surface temperature sensor 4 detects the external surface temperature of the section where the liquid working fluid accumulates when the heat-pipe phenomenon is completely caused in the main body part 2, the external surface temperature of the section of the main body part 2 that shows the temperature substantially equal to the dew point of the measurement space S1 can be directly detected by the first external surface temperature sensor 4. Because the dew point of the measurement space S1 can obtained without correcting the external surface temperature detected by the first external surface temperature sensor 4, the relative humidity of the measurement space S1 can be obtained with a higher degree of accuracy.

In the hygrometer according to the first embodiment, the computation unit 10a calculates the temperature difference between the external surface temperature of the section of the main body part 2 where the working fluid evaporates and the external surface temperature of the section where the gaseous working fluid is condensed, on the basis of the result of the detection of the external surface temperature detected by the first external surface temperature sensor 4 and the result of the detection of the external surface temperature detected by the second external surface temperature sensor 6. Therefore, it is possible to determine whether the heat-pipe phenomenon is completely caused in the main body part 2, on the basis of the difference in the calculated external surface temperature between the section of the main body part 2 where the working fluid evaporates and the section where the gaseous working fluid is condensed. As long as the fact that the heat-pipe phenomenon is completely caused in the main body part 2 can be confirmed, the fact that the dew point of the measurement space S1 is detected by the first external surface temperature sensor 4 accurately can be confirmed, and, as a result, the fact that the relative humidity of the measurement space S1 is detected accurately can be confirmed. On the other hand, when the difference in the calculated external surface temperature between the section of the main body part 2 where the working fluid evaporates and the section where the gaseous working fluid is condensed is less than the temperature difference at which the main body part 2 serving as the heat pipe exerts its maximum heat transfer amount, a gap occurs between the temperature detected by the first external surface temperature sensor 4 and the dew point of the measurement space S1. In this case, temperature control can be performed so that the section where the working fluid evaporates and the section where the gaseous working fluid is condensed generate the temperature difference at which the main body part 2 exerts its maximum heat transfer amount, whereby the first external surface temperature sensor 4 can accurately detect the dew point of the measurement space S1.

(Second Embodiment)

Figure 4:
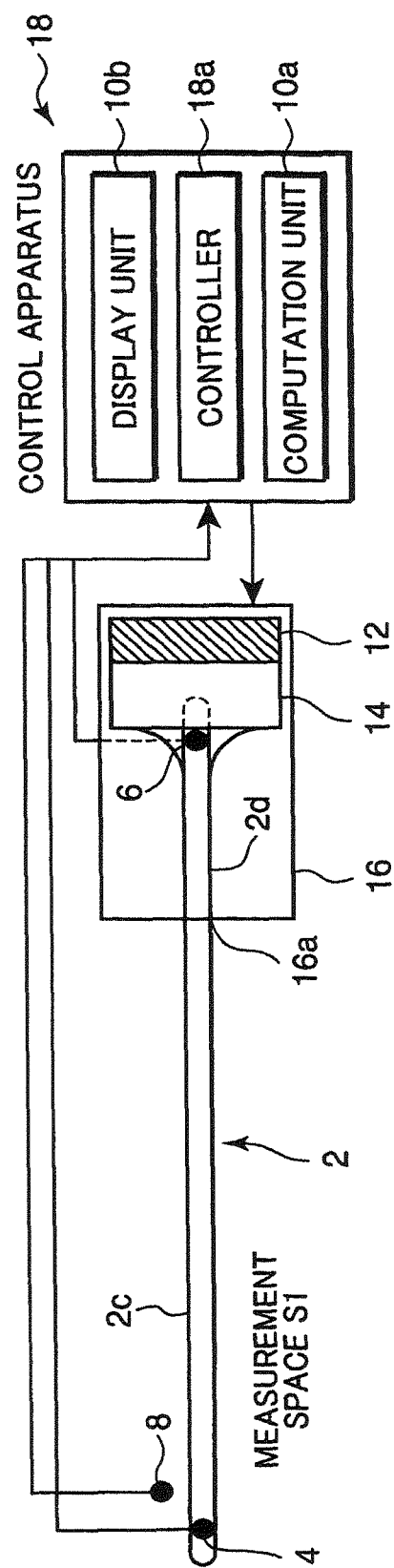
FIG. 4 is a block diagram for explaining the functions of the hygrometer according to a second embodiment of the present invention.

Next, the configuration of a hygrometer according to the second embodiment of the present invention is described with reference to FIG. 4.

Unlike the hygrometer according to the first embodiment described above, the hygrometer of the second embodiment is designed to forcibly cool a base side part 2d of the main body part 2 where the gaseous working fluid is condensed.

Specifically, the hygrometer according to the second embodiment has the main body part 2, the first external surface temperature sensor 4, the second external surface temperature sensor 6, the space temperature sensor 8, a peltier element 12, a connection part 14, a heat-insulating part 16, and control apparatus 18.

The functions and the configurations of the main body part 2, first external surface temperature sensor 4, second external surface temperature sensor 6, and space temperature sensor 8 according to the second embodiment are the same as those of the main body part 2, first external surface temperature sensor 4, second external surface temperature sensor 6, and space temperature sensor 8 in the first embodiment. However, while the first external surface temperature sensor 4 is attached to an external surface in the vicinity of an end part of a front side part 2c of the main body part 2 where the working fluid evaporates, the second external surface temperature sensor 6 is attached to an external surface in the vicinity of an end part of the base side part 2d of the main body part 2 where the gaseous working fluid is condensed. Here, as described hereinafter, the front side part 2c is a section in the main body part 2 that is one side of the heat-insulating part 16 fitted externally to the main body part 2, while the base side part 2d is a section in the main body part 2 that is on the other side of the heat-insulating part 16.

The peltier element 12 has a heat absorption part and a heat release part, wherein the heat absorption part performs a heat absorption operation in accordance with an input power, while the heat release part performs a heat release operation. The heat absorption part of the peltier element 12 is connected to the end part of the base side part 2d of the main body part 2. The heat absorption part of the peltier element 12 functions as a cooling part for cooling the base side part 2d and condensing the gaseous working fluid. This cooling action of the heat absorption part of the peltier element 12 forcibly cools the base side part 2d to the temperature lower than that of the front side part 2c disposed in the measurement space S1, whereby the heat-pipe phenomenon is completely caused in the main body part 2. The heat release part of the peltier element 12, on the other hand, serves to release the heat generated by heat exchange with the heat absorption part.

The base side part 2d of the main body part 2 and the peltier element 12 are joined to each other by the connection part 14. This connection part 14 rigidly joins and thermally connects the base side part 2d and the heat absorption part of the peltier element 12.

The heat-insulating part 16 is provided to cover the surroundings of the base side part 2d of the main body part 2, the second external surface temperature sensor 6, the peltier element 12, and the connection part 14. This heat-insulating part 16 is provided with a though-hole 16a into which the main body part 2 is inserted. Specifically, the front side part 2c of the main body part 2 is disposed under an atmosphere of the measurement space S1, and a part of a wall part configuring the heat-insulating part is fitted externally to the main body part 2 at a position between the front side part 2c and the base side part 2d within the heat-insulating part 16. The temperature within the heat-insulating part 16 can be kept lower than the temperature of the measurement space S1 by this heat-insulating part 16.

The signal output from the first external surface temperature sensor 4, the signal output from the second external surface temperature sensor 6, and the signal output from the space temperature sensor 8 are input to the control apparatus 18. The control apparatus 18 has the computation unit 10*a*, the display unit 10*b*, and a controller 18*a*.

The functions of the computation unit 10*a* and the display unit 10*b* are the same as the functions of the computation unit 10*a* and the display unit 10*b* described in the first embodiment. The controller 18*a* controls the peltier element 12 based on the difference in the external surface temperature of the main body part 2 that is calculated by the computation unit 10*a* on the basis of the signal from the first external surface temperature sensor 4 and the signal from the second external surface temperature sensor 6, that is, the temperature difference between the external surface temperature of the section in the front side part 2*c* where the working fluid evaporates and the external surface temperature of the section in the base side part 2*d* where the gaseous working fluid is condensed. More specifically, the controller 18*a* controls the cooling capacity of the heat absorption part of the peltier element 12 to cool the base side part 2*d*, so that the temperature difference at which the heat-pipe phenomenon is completely caused in the main body part 2 is generated between the external surface temperature of the section in the vicinity of the end part of the base side part 2*d* and the external surface temperature of the section in the vicinity of the end part of the front side part 2*c*.

The operation of the hygrometer according to the second embodiment is described next.

In the hygrometer according to the second embodiment, the front side part 2*c* of the main body part 2, the first external surface temperature sensor 4, and the space temperature sensor 8 are disposed under the atmosphere of the measurement space S1. Then, based on the signal output from the first external surface temperature sensor 4 and the signal output from the second external surface temperature sensor 6, the computation unit 10*a* calculates the temperature difference between the external surface temperature of the section in the vicinity of the end part of the front side part 2*c* of the main body part 2 and the external surface temperature of the section in the vicinity of the end part of the base side part 2*d*. Thereafter, based on the calculated temperature difference, the controller 18*a* controls the cooling capacity of the heat absorption part of the peltier element 12. At this moment, the base side part 2*d* is cooled such that a predetermined temperature difference is generated between the external surface temperature of the section in the vicinity of the end part of the base side part 2*d* and the external surface temperature of the section in the vicinity of the end part of the front side part 2*c*. As a result, the heat-pipe phenomenon is completely caused in the main body part 2, and, as with the first embodiment described above, the external surface temperature of the section in the vicinity of the end part of the front side part 2*c* of the main body part 2, that is, the section where the working fluid evaporates, becomes substantially equal to the dew point of the measurement space S1. As with the first embodiment described above, the computation unit 10*a* calculates the relative humidity of the measurement space S1 based on the signal from the first external surface temperature sensor 4 and the signal from the space temperature sensor 8, and the relative humidity and the temperature of the measurement space S1 are displayed on the display unit 10*b*.

As described above, according to the hygrometer of the second embodiment, in the main body part 2 installed in the measurement space S1, the space where the front side part 2*c* is located and the space where the base side part 2*d* is located are spaced from each other by the heat-insulating part 16, and the base side part 2*d* is cooled by the heat absorption part of the peltier element 12 to the temperature lower than that of the front side part 2*c*, whereby the external surface temperature of the section in the front side part 2*c* of the main body part 2 where the working fluid evaporates becomes substantially equal to the dew point of the measurement space S1. Because the first external surface temperature sensor 4 detects the external surface temperature of the section where the working fluid evaporates, the computation unit 10*a* can calculate the relative humidity of the measurement space S1 based on the detected external surface temperature of the section where the working fluid evaporates and the temperature of the measurement space S1 that is detected by the space temperature sensor 8. Therefore, as with the hydrometer according to the first embodiment, because the hygrometer of the second embodiment does not require a wick, the workload of maintaining the hydrometer can be alleviated.

Unlike the conventional mirror-surface condensing dew-point instrument configured by a large number of constituent parts, the hygrometer according to the second embodiment can be structurally simplified because it is configured by the main body part 2 where the heat-pipe phenomenon is caused, the first external surface temperature sensor 4, the second external surface temperature sensor 6, the space temperature sensor 8, the peltier element 12, the connection part 14, the heat-insulating part 16, and the control apparatus 18. Therefore, as with the hydrometer according to the first embodiment, the hygrometer according to the second embodiment can be structurally simplified, while alleviating the workload of its maintenance.

The hygrometer according to the second embodiment has the peltier element 12 capable of cooling the base side part 2*d* of the main body part 2, and the heat-insulating part 16 capable of separating the space where the front side part 2*c* of the main body part 2 is located from the space where the base side part 2*d* is located. Thus, it is possible to forcibly cool the base side part 2*d* and keep the temperature of the base side part 2*d* low, and thereby it is possible to forcibly completely cause the heat-pipe phenomenon in the main body part 2. Because the hygrometer is not subjected to the installation limitation where the main body part is disposed across the two spaces having a predetermined temperature difference, a hygrometer that can be applied under a wider variety of conditions can be configured.

Further, in the hygrometer according to the second embodiment, the cooling part for cooling the base side part 2*d* of the main body part 2 is configured by the heat absorption part of the peltier element 12. Because the peltier element 12 is activated by a small amount of electricity, the hygrometer of the second embodiment can cool the base side part 2*d* of the main body part 2 while preventing power consumption.

In the hygrometer according to the second embodiment, the cooling capacity of the heat absorption part of the peltier element 12 is controlled based on the temperature difference between the external surface temperature of the section of the main body part 2 where the working fluid evaporates and the external surface temperature of the section where the gaseous working fluid is condense, the temperature difference being calculated by the computation unit 10*a*. Thus, the difference in the external surface temperature between the section of the main body part 2 where the working fluid evaporates and the section where the gaseous working fluid is condensed can be set at the temperature difference at which the heat-pipe phenomenon is completely caused in the main body part 2.

(Third Embodiment)

Next, the configuration of a dew-point instrument according to the third embodiment of the present invention is described with reference to FIG. 5.

Figure 5:
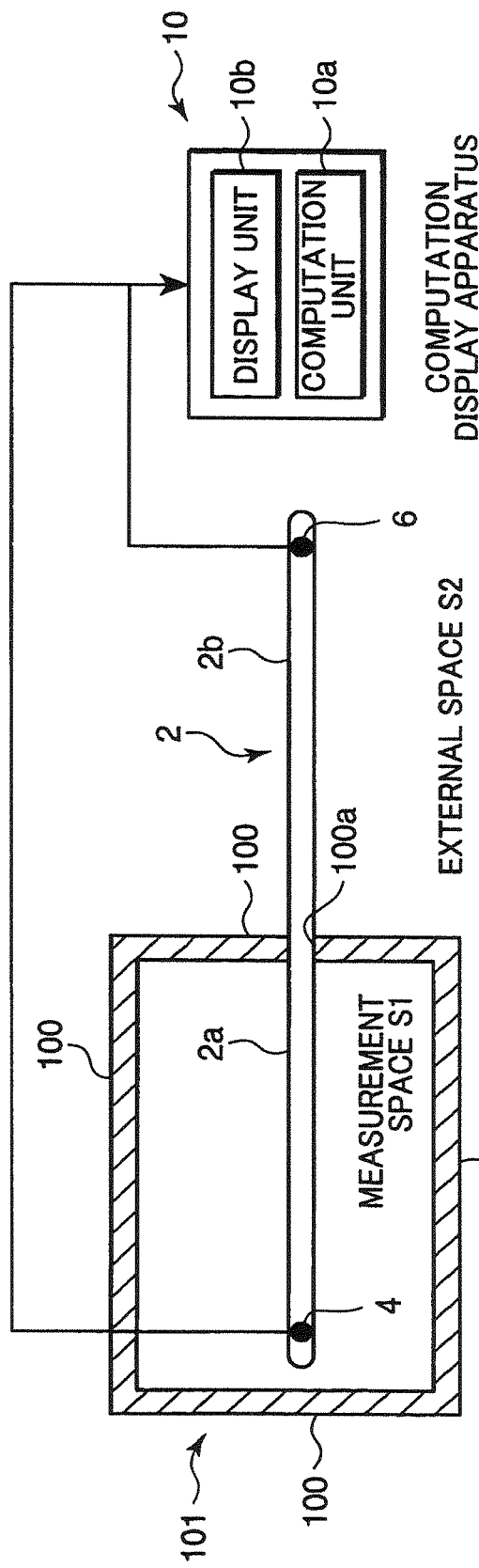
FIG. 5 is a block diagram for explaining the functions of a dew-point instrument according to a third embodiment of the present invention.

The dew-point instrument according to the third embodiment is for measuring the dew point of the measurement space S1, and has a configuration without the space temperature sensor 8 (see FIG. 2) of the hygrometer of the first embodiment, as shown in FIG. 5. The dew-point instrument has the same principle as the hygrometer of the first embodiment, in which the external surface temperature in the vicinity of the end part of the internal part 2a of the main body part 2 where the heat-pipe phenomenon is caused, that is, the external surface temperature of the section where the working fluid evaporates, becomes substantially equal to the dew point of the measurement space S1. The external surface temperature of the section of the internal part 2a where the working fluid evaporates is detected by the first external surface temperature sensor 4, and the dew point of the measurement space S1 is displayed on the display unit 10b of the computation display apparatus 10 in response to the signal output from the first external surface temperature sensor 4. Unlike the first embodiment, in the third embodiment the computation unit 10a does not compute the relative humidity described above. In other words, the computation unit 10a in the third embodiment computes only the temperature difference between the external surface temperature of the section of the internal part 2a where the working fluid evaporates and the external surface temperature of the section of the external part 2b where the gaseous working fluid is condensed, based on the signal from the first external surface temperature sensor 4 and the signal from the second external surface temperature sensor 6. The rest of the configuration of the dew-point instrument according to the third embodiment is same as the configuration of the hygrometer according to the first embodiment.

As described above, in the dew-point instrument according to the third embodiment, the external surface temperature of the section on the measurement space S1 side of the main body part 2 where the working fluid evaporates becomes substantially equal to the dew point of the measurement space S1, as with the case in the hygrometer according to the first embodiment. Therefore, the dew point of the measurement space S1 can be obtained by causing the first external surface temperature sensor 4 to detect the external surface temperature of the section where the working fluid evaporates. Therefore, as with the hygrometer according to the first embodiment, because the dew-point instrument of the third embodiment does not require a wick, the workload of maintaining the dew-point instrument can be alleviated.

Moreover, unlike the conventional mirror-surface condensing dew-point instrument configured by a large number of constituent parts, the dew-point instrument according to the third embodiment can be structurally simplified because it is configured by the main body part 2 where the heat-pipe phenomenon is caused, the first external surface temperature sensor 4, the second external surface temperature sensor 6, and the computation display apparatus 10. Therefore, this dew-point instrument can be structurally simplified, while alleviating the workload of its maintenance.

The rest of the effects of the dew-point instrument according to the third embodiment are the same as the effects of the hygrometer of the first embodiment.

(Fourth Embodiment)

Next, the configuration of a dew-point instrument according to the fourth embodiment is described with reference to FIG. 6.

Figure 6:
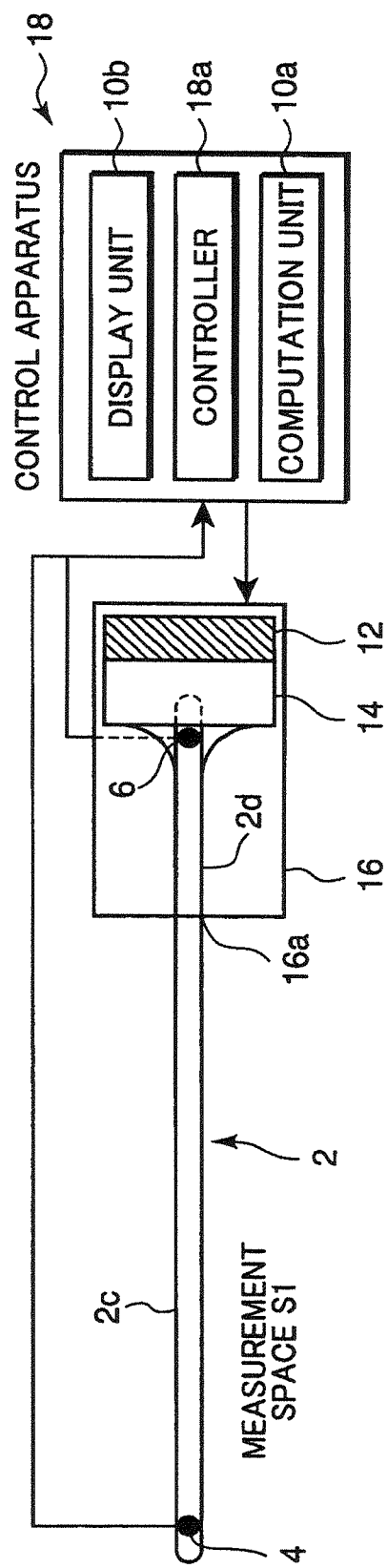
FIG. 6 is a block diagram for explaining the functions of a dew-point instrument according to a fourth embodiment of the present invention.

The dew-point instrument according to the fourth embodiment is for measuring the dew point of the measurement space S1, and has a configuration without the space temperature sensor 8 (see FIG. 4) of the hygrometer of the second embodiment, as shown in FIG. 6. As with the hygrometer according to the second embodiment, in this dew-point instrument the heat absorption part of the peltier element 12 forcibly cools the base side part 2d of the main body part 2 where the gaseous working fluid is condensed. Further, as with the second embodiment, the computation unit 10a calculates the temperature difference between the external surface temperature of the section in the vicinity of the end part of the front side part 2c of the main body part 2 and the external surface temperature of the section in the vicinity of the end part of the base side part 2d, and then the controller 18a controls the cooling capacity of the heat absorption part of the peltier element 12 on the basis of the calculated temperature difference. At this moment, the base side part 2d is cooled such that the temperature difference at which the heat-pipe phenomenon is completely caused in the main body part 2 is generated between the external surface temperature of the section in the vicinity of the end part of the base side part 2d and the external surface temperature of the section in the vicinity of the end part of the front side part 2c. As a result, the heat-pipe phenomenon is completely caused in the main body part 2, and the external surface temperature of the section in the vicinity of the end part of the front side part 2c of the main body part 2, that is, the external surface temperature of the section where the working fluid evaporates, becomes substantially equal to the dew point of the measurement space S1, as with the second embodiment. Then, the external surface temperature of the section in the front side part 2c where the working fluid evaporates is detected by the first external surface temperature sensor 4, and the dew point of the measurement space S1 is displayed on the display unit 10b of the control apparatus 18 in response to the signal that is output from the first external surface temperature sensor 4. The rest of the configuration of the dew-point instrument according to the fourth embodiment is same as the configuration of the hygrometer according to the second embodiment.

As described above, as with the hygrometer according to the second embodiment, in the dew-point instrument of the fourth embodiment the external surface temperature of the section in the front side part 2c of the main body part 2 where the working fluid evaporates becomes substantially equal to the dew point of the measurement space S1. Consequently, the dew point of the measurement space S1 can be obtained by causing the first external surface temperature sensor 4 to detect the external surface temperature of the section where the working fluid evaporates. Therefore, as with the hygrometer according to the second embodiment, because the dew-point instrument of the fourth embodiment does not require a wick, the workload of maintaining the dew-point instrument can be alleviated.

Unlike the conventional mirror-surface condensing dew-point instrument configured by a large number of constituent parts, the dew-point instrument according to the fourth embodiment can be structurally simplified because it is configured by the main body part 2 where the heat-pipe phenomenon is caused, the first external surface temperature sensor 4, the second external surface temperature sensor 6, the peltier element 12, the connection part 14, the heat-insulating part 16, and the control apparatus 18. Therefore, this dew-point instrument can be structurally simplified, while alleviating the workload of its maintenance.

The rest of the effects of the dew-point instrument according to the fourth embodiment are the same as the effects of the hygrometer of the second embodiment.

Note that the embodiments disclosed herein are merely examples in all respects and should not be considered restrictive.

The scope of the present invention is defined by the scope of claims rather than by the above description of the embodiments, and includes meanings equivalent to those of the scope of claims and any modification within the scope of claims.

For example, in each of the embodiments described above, although the first external surface temperature sensor 4 detects the external surface temperature of the section in the vicinity of the end part of the internal part 2a or front side part 2c of the main body part 2 where the working fluid evaporates, the present invention is not limited to this configuration. Specifically, the first external surface temperature sensor 4 may be attached to the external surface of a predetermined section other than those above of the main body part 2 to detect the external surface temperature of this section. In this case, the temperature difference is generated between the temperature detected by the first external surface temperature sensor 4 and the external surface temperature of the section where the working fluid evaporates, i.e., the dew point of the measurement space S1. Thus, correction part is provided in addition to the first external surface temperature sensor 4, and the temperature difference is measured beforehand, so that the dew point of the measurement space S1 can be obtained by causing the correction part to correct the temperature which the first external surface temperature sensor 4 detects by the temperature difference. As the section to which the first external surface temperature sensor 4 is attached, for example, the first external surface temperature sensor 4 may be attached to the external part 2b located in the external space S2 of the main body part 2 in the configurations described in the first and third embodiments. In addition, in the configurations described in the second and fourth embodiments, the first external surface temperature sensor 4 may be attached to the base side part 2d located within the heat-insulating part 16. In this aspect, the first temperature deriving part of the present invention is configured by the first external surface temperature sensor 4 and the correction part.

In each of the embodiments described above, although the first external surface temperature sensor 4 and the second external surface temperature sensor 6 are directly attached to the external surface of the main body part 2 to detect the external surface temperature, the present invention is not limited thereto, and a temperature sensor for detecting the external surface temperature of the main body part 2 in a non-contact state may be used without directly attaching the first external surface temperature sensor 4 and the second external surface temperature sensor 6 to the main body part 2.

In each of the embodiments described above, the first external surface temperature sensor 4 is attached to the external surface of the section in the internal part 2a or front side part 2c of the main body part 2 where the working fluid evaporates, but, instead, a first internal surface temperature sensor serving as the first temperature deriving part of the present invention may be attached to an internal surface of the section in the main body part 2 where the working fluid evaporates, to detect the internal surface temperature of this section and to calculate the dew point and humidity of the measurement space S1 on the basis of this internal surface temperature. Because it is considered that the internal surface temperature of the section in the main body part 2 where the working fluid evaporates represents the dew point of the measurement space S1 more accurately than the external surface temperature of this section does, the humidity of the measurement space S1 can be obtained more accurately in this case. Moreover, when attaching the first internal surface temperature sensor to the internal surface of the main body part 2, as with the case where the first external surface temperature sensor 4 is attached to the external surface of the main body part 2, the first internal surface temperature sensor may be attached to the internal surface of the other predetermined section in the main body part 2 where the working fluid evaporates. In this case, however, similarly, the correction part for correcting the temperature difference between the temperature detected by the first internal surface temperature sensor and the internal surface temperature of the section where the working fluid evaporates needs to be provided. Specifically, in this aspect, the first temperature deriving part according to the present invention is configured by the first internal surface temperature sensor and the correction part.

In addition, in each of the embodiments described above, the second external surface temperature sensor 6 is attached to the external surface of the section in the external part 2b or base side part 2d of the main body part 2 where the gaseous working fluid is condensed, to detect the external surface temperature of this section, but, instead, a second internal surface temperature sensor serving as the second temperature deriving part of the present invention may be attached to an internal surface of the section of the main body part 2 where the gaseous working fluid is condensed, to detect the internal surface temperature of this section.

In each of the embodiments described above, although the main body part 2 is configured as a heat pipe, the main body part 2 may be configured by a meandering capillary tube type heat pipe or an oscillating heat pipe known as a heat lane™.

In the second and fourth embodiments, although the heat absorption part of the peltier element 12 is used as the cooling part of the present invention, a constituent part other than the peltier element may be used as the cooling part.

In the hygrometer and the dew-point instrument according to each of the embodiments described above, the second external surface temperature sensor 6 is provided, but when it is not necessary to confirm the difference between the external surface temperature of the section in the main body part 2 where the working fluid evaporates and the external surface temperature of the section where the gaseous working fluid is condensed, the second external surface temperature sensor 6 may be omitted. For example, when the temperature of the measurement space S1 is already known as with that of the temperature and humidity chamber 101, the temperature difference between the measurement space S1 and the external space S2 can be obtained. Therefore, from this temperature difference, it can be roughly understood whether or not the temperature difference at which the heat-pipe phenomenon is caused in the main body part 2 is generated between the external surface temperature of the section in the internal part 2a of the main body part 2 where the working fluid evaporates and the external surface temperature of the section in the external part 2b where the gaseous working fluid is condensed. In this case, because there is no problem in particularly confirming the difference between the external surface temperatures of both sections, the second external surface temperature sensor 6 can be omitted.

Further, the first and third embodiments have described an example in which the internal part 2a of the main body part 2 is disposed on the lower side and the external part 2b of the main body part 2 is disposed on the upper side, the present invention is not limited to this configuration. Specifically, when the heat-pipe phenomenon is caused in the main body part 2, the internal part 2a may be disposed on the upper side and the external part 2b may be disposed on the lower side, or the main body part 2 may be disposed horizontally without having the vertical relationship between the internal part 2a and the external part 2b. Similarly, the relative positions between the front side part 2c and the base side part 2d of the main body part 2 according to the second and fourth embodiments may be arranged in any way.

(Summary of the Embodiments)

The summary of the embodiments is described hereinafter.

Specifically, the hygrometer according to the first embodiment is a hygrometer for measuring the relative humidity of the measurement space, the hygrometer having: a main body part that is configured to encapsulate the working fluid therein and to cause the heat-pipe phenomenon and disposed across the measurement space and an external space that is spaced from the measurement space by a heat-insulating part and has a temperature lower than that of the measurement space; first temperature deriving part for deriving a temperature of the main body part in a section where the working fluid evaporates; a space temperature detecting unit for detecting a temperature of the measurement space; and a computation unit for calculating the relative humidity of the measurement space based on the temperature of the main body part derived by the first temperature deriving part and the temperature of the measurement space detected by the space temperature detecting unit.

As a result of the keen investigation, the inventor of the present application has discovered that, by disposing the main body part where the heat-pipe phenomenon is caused across the two spaces spaced from each other by the heat-insulating part, and by making the temperature of the end part of the main body part located in one of the spaces lower than the temperature of the end part located in the other space, the temperature of the section in the other space of the main body part where the working fluid evaporates becomes substantially equal to the dew point of the other space.

Therefore, in the hygrometer according to the first embodiment, the main body part where the heat-pipe phenomenon is caused is disposed across the measurement space and the external space colder than the measurement space, the measurement space and the external space being spaced from each other by the heat-insulating part. Therefore, working fluid evaporates on the measurement space side of the main body part, and the temperature of the main body part in the section where the working fluid evaporates becomes substantially equal to the dew point of the measurement space. Then, the temperature of the main body part in the section where the working fluid evaporates is derived by the first temperature deriving part. Thus, the computation unit can calculate the relative humidity of the measurement space on the basis of the derived temperature of the section where the working fluid evaporates and the temperature of the measurement space that is detected by the space temperature detecting unit. Therefore, unlike the conventional wet and dry bulb hygrometer, because the hygrometer of the first embodiment does not require a wick for humidity measurement, it is not necessary to carry out the troublesome work for replacing the wick every time when the wick becomes old and the force for pumping up the water is weakened. Therefore, the workload of maintaining the hygrometer can be alleviated.

Unlike the conventional mirror-surface condensing dew-point instrument configured by a large number of constituent parts, the hygrometer can be structurally simplified because it is configured by the main body part where the heat-pipe phenomenon is caused, the first temperature deriving part, the space temperature detecting unit, and the computation unit. Therefore, the hygrometer according to the first embodiment can be structurally simplified, while alleviating the workload of its maintenance.

The hygrometer according to the second embodiment is a hygrometer for measuring the relative humidity of the measurement space, the hygrometer having: a main body part that is installed in the measurement space and configured to encapsulate a working fluid therein and to cause a heat-pipe phenomenon; a heat-insulating part fitted externally to the main body part; a cooling part for cooling a base side part on one side of the main body part in relation to the heat-insulating part and thereby condensing the working fluid that evaporates into gas in a front side part on the other side of the main body part in relation to the heat-insulating part; first temperature deriving part for deriving a temperature of the main body part in a section where the working fluid evaporates; a space temperature detecting unit for detecting a temperature of the measurement space; and a computation unit for calculating the relative humidity of the measurement space based on the temperature of the main body part derived by the first temperature deriving part and the temperature of the measurement space detected by the space temperature detecting unit.

As described above, by disposing the main body part where the heat-pipe phenomenon is caused across the two spaces spaced from each other by the heat-insulating part, and by making the temperature of the end part of the main body part located in one of the spaces lower than the temperature of the end part located in the other space, the temperature of the section in the other space of the main body part where the working fluid evaporates becomes substantially equal to the dew point of the other space. Therefore, according to the hygrometer of the second embodiment, in the main body part installed in the measurement space, the space where the front side part is located and the space where the base side part is located are spaced from each other by the heat-insulating part, and the base side part is cooled by the cooling part and thereby becomes colder than the front side part. Accordingly, the working fluid evaporates in the front side part of the main body part, and the temperature of the main body part in this section where the working fluid evaporates becomes substantially equal to the dew point of the measurement space. Since the temperature of the main body part in the section where the working fluid evaporates is derived by the first temperature deriving part, the computation unit can calculate the relative humidity of the measurement space on the basis of the derived temperature of the section where the working fluid evaporates and the temperature of the measurement space that is detected by the space temperature detecting unit. Therefore, unlike the conventional wet and dry bulb hygrometer, because the hygrometer of the second embodiment does not require a wick for humidity measurement, it is not necessary to carry out the troublesome work for replacing the wick every time when the wick becomes old and the force for pumping up the water is weakened. Therefore, the workload of maintaining the hygrometer can be alleviated.

Unlike the conventional mirror-surface condensing dew-point instrument configured by a large number of constituent parts, the hygrometer can be structurally simplified because it is configured by the main body part where the heat-pipe phenomenon is caused, the first temperature deriving part, the space temperature detecting unit, the cooling part, the heat-insulating part, and the computation unit. Therefore, this hygrometer can be structurally simplified, while alleviating the workload of its maintenance. In addition, since this hygrometer has the cooling part for cooling the base side part of the main body part and the heat-insulating part capable of separating the space where the front side part of the main body part is located from the space where the base side part is located, it is possible to forcibly cool the base side part of the main body part and keep the temperature of the base side part low, and thereby it is possible to forcibly cause the heat-pipe phenomenon in the main body part. Because the hygrometer is not subjected to the installation limitation where the main body part is disposed across the two spaces having a predetermined temperature difference, a hygrometer that can be applied under a wider variety of conditions can be configured.

In this case, it is preferred that the cooling part is configured by the heat absorption part of the peltier element. Because the peltier element is activated by a small amount of electricity, this configuration can cool the base side part of the main body part while preventing power consumption.

In the hygrometer described above, the main body part may be configured by a heat pipe, a meandering capillary tube type heat pipe, or an oscillating heat pipe.

In the hygrometer, it is preferred that the first temperature deriving part derive the temperature of the section where the working fluid in liquid form accumulates when the heat-pipe phenomenon is completely caused in the main body part.

With this configuration, the first temperature deriving part can directly derive the temperature of the section that indicates the temperature substantially equal to the dew point of the measurement space of the main body part. Because the dew point of the measurement space can be obtained from the temperature derived by the first temperature deriving part without performing much correction, the relative humidity of the measurement space can be obtained with a higher degree of accuracy.

It is preferred that the hygrometer described above have the second temperature deriving part for deriving a temperature of the main body part in a section where the working fluid in gaseous form is condensed, and that the computation unit calculates the temperature difference between the temperature of the section in the main body part where the working fluid evaporates and the temperature of the section where the working fluid in gaseous form is condensed, based on the result of deriving the temperature by means of the first temperature deriving part and the result of deriving the temperature by means of the second temperature deriving part.

With this configuration, whether the heat-pipe phenomenon is completely caused in the main body part can be determined based on the calculated difference in temperature between the section of the main body part where the working fluid evaporates and the section where the gaseous working fluid is condensed. In addition, according to the configuration having the cooling part for cooling the base side part of the main body part, the cooling part is controlled based on the calculated temperature difference, whereby the difference in temperature between the section of the main body part where the working fluid evaporates and the section where the gaseous working fluid is condensed can be set at the temperature difference at which the heat-pipe phenomenon is completely caused in the main body part.

The dew-point instrument according to the third embodiment is a dew-point instrument for measuring the dew point of the measurement space, the dew-point instrument having: a main body part that is configured to encapsulate the working fluid therein and to cause the heat-pipe phenomenon and disposed across the measurement space and an external space that is spaced from the measurement space by a heat-insulating part and has a temperature lower than that of the measurement space; and first temperature deriving part for deriving a temperature of the main body part in a section where the working fluid evaporates.

The dew-point instrument has the same principle as the hygrometer in which the main body is disposed across the measurement space and the external space, wherein the temperature of the section in the measurement space of the main body part where the working fluid evaporates becomes substantially equal to the dew point of the measurement space. Therefore, the dew point of the measurement space can be obtained by causing the first temperature deriving part to derive the temperature of the section where the working fluid evaporates. As with the hygrometer described above, because this dew-point instrument does not require a wick, the workload of maintaining the dew-point instrument can be alleviated.

Unlike the conventional mirror-surface condensing dew-point instrument configured by a large number of constituent parts, the dew-point instrument can be structurally simplified because it is configured by the main body part where the heat-pipe phenomenon is caused and the first temperature deriving part. Therefore, this dew-point instrument can be structurally simplified, while alleviating the workload of its maintenance.

The dew-point instrument according to the fourth embodiment is a dew-point instrument for measuring the dew point of the measurement space, having: a main body part that is installed in the measurement space and configured to encapsulate a working fluid therein and to cause a heat-pipe phenomenon; a heat-insulating part fitted externally to the main body part; a cooling part for cooling a base side part on one side of the main body part in relation to the heat-insulating part and thereby condensing the working fluid that evaporates into gas in a front side part on the other side of the main body part in relation to the heat-insulating part; and first temperature deriving part for deriving a temperature of the main body part in a section where the working fluid evaporates.

The dew-point instrument has the same principle as the hygrometer having the cooling part, wherein the temperature of the section in the front side part of the main body part where the working fluid evaporates becomes substantially equal to the dew point of the measurement space. Therefore, the dew point of the measurement space can be obtained by causing the first temperature deriving part to derive the temperature of the section where the working fluid evaporates. As with the hygrometer described above, because this dew-point instrument does not require a wick, the workload of maintaining the dew-point instrument can be alleviated.

Unlike the conventional mirror-surface condensing dew-point instrument configured by a large number of constituent parts, this dew-point instrument can be structurally simplified because it is configured by the main body part where the heat-pipe phenomenon is caused, the first temperature deriving part, the cooling part, and the heat-insulating part. Therefore, this dew-point instrument can be structurally simplified, while alleviating the workload of its maintenance.

In addition, since this dew-point instrument has the cooling part for cooling the base side part of the main body part and the heat-insulating part capable of separating the space where the front side part of the main body part is located from the space where the base side part is located, it is possible to forcibly cool the base side part of the main body part and keep the temperature of the base side part low, and thereby it is possible to forcibly cause the heat-pipe phenomenon in the main body part. Because the dew-point instrument is not subjected to the installation limitation where the main body part is disposed across the two spaces having a predetermined temperature difference in order to cause the heat-pipe phenomenon in the main body part, a dew-point instrument that can be applied under a wider variety of conditions can be configured.

In this case, it is preferred that the cooling part is configured by the heat absorption part of the peltier element. Because the peltier element is activated by a small amount of electricity, this configuration can cool the base side part of the main body part while preventing power consumption.

In the dew-point instrument described above, the main body part may be configured by a heat pipe, a meandering capillary tube type heat pipe, or an oscillating heat pipe.

In the dew-point instrument described above, it is preferred that the first temperature deriving part derive the temperature of the section where the working fluid in liquid form accumulates when the heat-pipe phenomenon is completely caused in the main body part.

With this configuration, the first temperature deriving part can directly derive the temperature of the section that indicates the temperature substantially equal to the dew point of the measurement space of the main body part. Because the dew point of the measurement space can be obtained from the temperature derived by the first temperature deriving part without performing much correction, the dew point of the measurement space can be obtained with a higher degree of accuracy.

It is preferred that the dew-point instrument has: second temperature deriving part for deriving a temperature of the main body part in a section where the working fluid in gaseous form is condensed; and a computation unit that calculates the temperature difference between the temperature of the section in the main body part where the working fluid evaporates and the temperature of the section where the working fluid in gaseous form is condensed, based on the result of deriving the temperature by means of the first temperature deriving part and the result of deriving the temperature by means of the second temperature deriving part.

With this configuration, whether the heat-pipe phenomenon is completely caused in the main body part can be determined based on the calculated difference in temperature between the section of the main body part where the working fluid evaporates and the section where the gaseous working fluid is condensed. In addition, according to the configuration having the cooling part for cooling the base side part of the main body part, the cooling part is controlled based on the calculated temperature difference, whereby the difference in temperature between the section of the main body part where the working fluid evaporates and the section where the gaseous working fluid is condensed can be set at the temperature difference at which the heat-pipe phenomenon is completely caused in the main body part.

What is claimed is:

1. A dew-point instrument for measuring a dew point of a measurement space defined by a heat-insulating wall, the heat-insulating wall having a through-hole, the dew-point instrument comprising:
    a main body part that is configured to encapsulate a working fluid therein to cause a heat-pipe phenomenon and that is disposed across the through-hole of the heat-insulating wall so as to be in both the measurement space and an external space that is outside of the measurement space, a temperature of the external space being lower than that of the measurement space; and
    a first temperature deriving part for deriving a temperature of an evaporating section of the main body part, the evaporating section being where the working fluid evaporates due to the heat-pipe phenomenon, the temperature at the evaporating section being substantially equal to a dew point temperature of the measurement space.

2. The dew-point instrument according to claim 1, wherein the main body part is configured by a heat pipe.

3. The dew-point instrument according to claim 1, wherein the main body part is configured by a meandering capillary tube type heat pipe or an oscillating heat pipe.

4. The dew-point instrument according claim 1, wherein the first temperature deriving part derives the temperature of a section where the working fluid in liquid form accumulates when the heat-pipe phenomenon is completely caused in the main body part.

5. The dew-point instrument according to claim 1, further comprising:
    second temperature deriving part for deriving a temperature of the main body part in a section where the working fluid in gaseous form is condensed; and
    a computation unit that calculates a temperature difference between the temperature of the section in the main body part where the working fluid evaporates and the temperature of the section where the working fluid in gaseous form is condensed, based on a result of deriving the temperature by means of the first temperature deriving part and a result of deriving the temperature by means of the second temperature deriving part.

6. A temperature and humidity chamber that uses the dew-point instrument described in claim 1.

* * * * *